United States Patent [19]

Mas

[11] Patent Number: 5,016,659

[45] Date of Patent: May 21, 1991

[54] COMPACT MOUTH AND BREATH FRESHENER APPARATUS

[76] Inventor: Eduardo M. Mas, 1528 W. 222nd St., Torrance, Calif. 90501

[21] Appl. No.: 502,998

[22] Filed: Apr. 2, 1990

[51] Int. Cl.$^5$ ............................................. A61C 15/00
[52] U.S. Cl. ..................................... 132/321; 132/329
[58] Field of Search ............... 132/320, 321, 329, 333; 604/1, 11

[56]  References Cited

U.S. PATENT DOCUMENTS

| | | | |
|---|---|---|---|
| 808,606 | 12/1905 | Hamel | 132/321 X |
| 1,856,559 | 5/1932 | Johnson | 132/321 X |
| 2,035,425 | 3/1936 | Doll | 132/329 X |
| 2,760,628 | 8/1956 | Briggs | 132/329 X |
| 2,762,501 | 9/1956 | Cameron | 132/329 X |
| 3,078,856 | 2/1963 | Bender et al. | 132/321 |
| 4,795,421 | 1/1989 | Blasius, Jr. et al. | 604/1 |
| 4,887,994 | 12/1989 | Bedford | 132/320 X |

FOREIGN PATENT DOCUMENTS

| | | | |
|---|---|---|---|
| 2748343 | 5/1979 | Fed. Rep. of Germany | 132/321 |
| 1552868 | 9/1979 | United Kingdom | 132/329 |

Primary Examiner—John J. Wilson
Assistant Examiner—Jeffrey A. Smith
Attorney, Agent, or Firm—Thomas I. Rozsa

[57]  ABSTRACT

A compact mouth and breath freshening apparatus which includes a multiplicity of individual elongated members with each elongated member carrying a swab that has been impregnated with a mouth and breath freshening agent. The multiplicity of elongated members are aligned in one or more rows and incorporated on a support base which in turn is housed within a compact carrying case. Alternatively, the multiplicity of elongated members are supported by having their respective swabs retained in a wrapper which in turn is supported in a case.

21 Claims, 2 Drawing Sheets

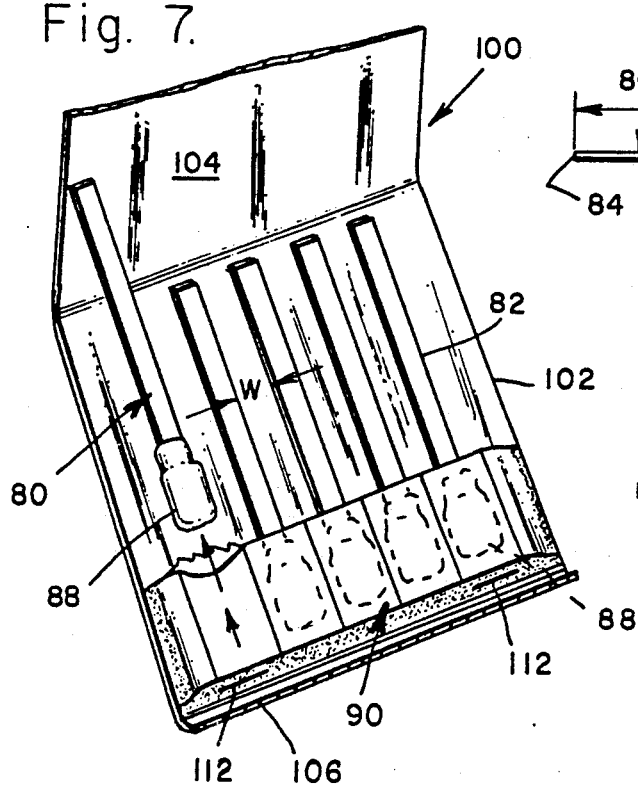
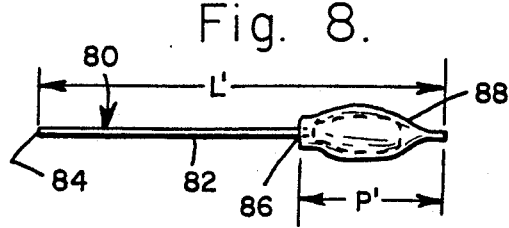
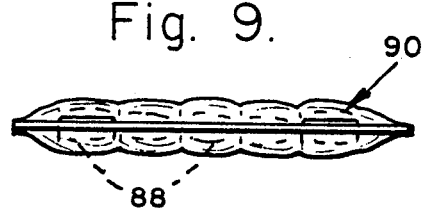
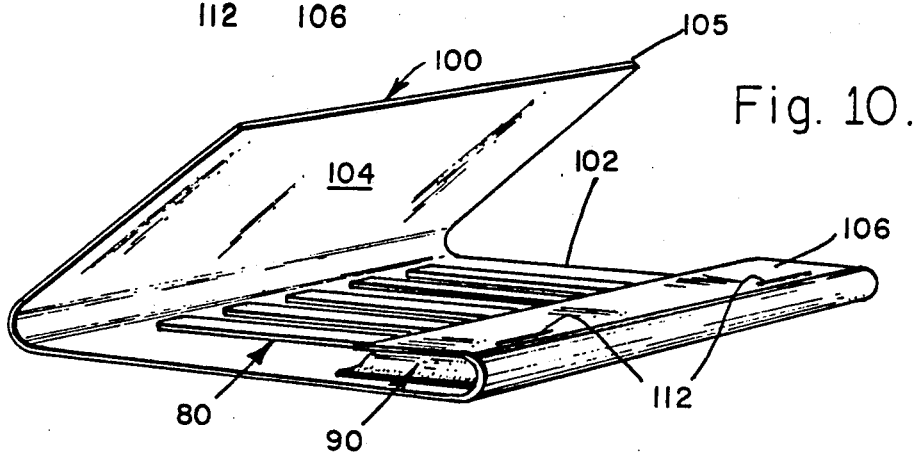
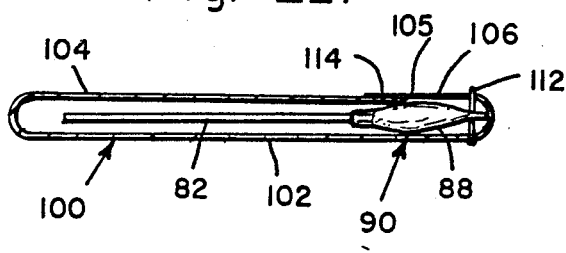

COMPACT MOUTH AND BREATH FRESHENER APPARATUS

BACKGROUND OF THE INVENTION

1. Field of the Invention

The present invention relates to the field of breath freshening and mouth freshening apparatus which are used to counteract bad breath and to freshen and sweeten the mouth. The invention further relates to non-liquid and non-aerosol freshening agents which are compact and can be easily carried in a coat pocket as well as a carrying element such as a pocketbook.

2. Description of the Prior Art

Most commonly, mouth and breath fresheners are in liquid form and are housed in a small vial made of plastic or comparable material. A shot of the liquid freshener is usually dispensed by an aerosol pump means or comparable dispensing apparatus. One major problem with such apparatus is that they are bulky and take up a large amount of room in the user's pocket or purse. A second major problem is that liquid from such dispensers may leak, thereby marring the pocket or container such as a purse in which they are carried.

Other type of breath and mouth fresheners consist of various breath mints, candies and gum. While avoiding the problem of the liquid fresheners, mints and candy add unwanted calories and also may enhance cavities in the user's teeth. Chewing gum also has an adverse effect on the user's teeth.

Accordingly, there is a significant need for a compact apparatus to be used to freshen and sweeten a user's breath and mouth while at the same time avoiding the problems associated with liquid fresheners, candies, mints and gum.

SUMMARY OF THE PRESENT INVENTION

The present invention relates to a compact mouth and breath freshening apparatus which is comprised of a multiplicity of individual elongated member with each elongated member carrying a swab that has been impregnated with a mouth and breath freshening agent. The multiplicity of elongated members are aligned in one or more rows and incorporated on a support base which in turn is housed within a compact carrying case. Alternatively, the multiplicity of elongated members can be supported by their respective heads in a plastic packet with their respective stems individually standing free and not incorporated onto a support base.

It has been discovered, according to the present invention, that a mouth and breath freshening agent can be incorporated into an individual elongated object such as a elongated member which carries a section of absorbant material at one end wherein the absorbant material has been impregnated with a breath freshening agent.

It has also been discovered, according to the present invention, that the elongated member may be made of thin strong plastic material such as mylar or cellophane and supported on a plastic base. The plastic base may support a multiplicity of such elongated members aligned in a row and the base may further support a multiplicity of rows of elongated members with elongated members in one row offset from adjacent picks in adjacent elongated members rows.

It has additionally been discovered, according to the present invention, that the elongated member may be made of thin strong material and the head carrying the gel can be encased in a plastic pouch which serves to support a multiplicity of elongated members in such manner, with each stem extending freely away from the pouch.

It has further been discovered, according to the present invention, that the absorbant material carried on the end of the elongated member may be made of cotton, velvet, or comparable material.

It has additionally been discovered, according to the present invention, that the multiplicity of elongated members having a portion thereof made of absorbant material impregnated with breath freshener can be carried in a compact case comparable to a matchbook which can be conveniently carried in any pocket or carrying apparatus such as a purse.

It is therefore an object of the present invention to provide a compact breath and mouth freshening apparatus in which a multiplicity of individual breath freshening applicators are carried.

It is another object of the present invention to provide a breath freshening apparatus which is non-liquid to thereby eliminate the bulkiness of liquid breath freshening dispensers and further eliminate the hazard of leaks from the liquid breath freshening dispenser.

It is a further object of the present invention to provide a breath freshening apparatus which provides a multiplicity of individual breath freshening applicators, each of which can be used and subsequently discarded, which applicators are all housed in a compact manner so that they are offset from one another and remain fresh for future use.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 7 is a perspective view of another alternative embodiment of he present invention with a multiplicity of individual breath freshening picks supported in a plastic pouch, with a separation between adjacent elongated members so that the head member including the breath freshening agent is supported in the pouch and the stem extends therefrom, with the plastic pouch retained in a case.

FIG. 8 is a cross-sectional view of an individual stick with the head member retained in a plastic pouch.

FIG. 9 is a cross-sectional view illustrating a multiplicity of elongated member heads retained in the plastic pouch.

FIG. 10 is a perspective view of the alternative embodiment present invention compact mouth and breath freshening apparatus with the cover in the opened position to illustrate a multiplicity of mouth and breath freshening elongated members retained therein.

FIG. 11 is a side elevational view of the alternative embodiment present invention compact mouth and breath freshening apparatus with the cover in the closed position.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
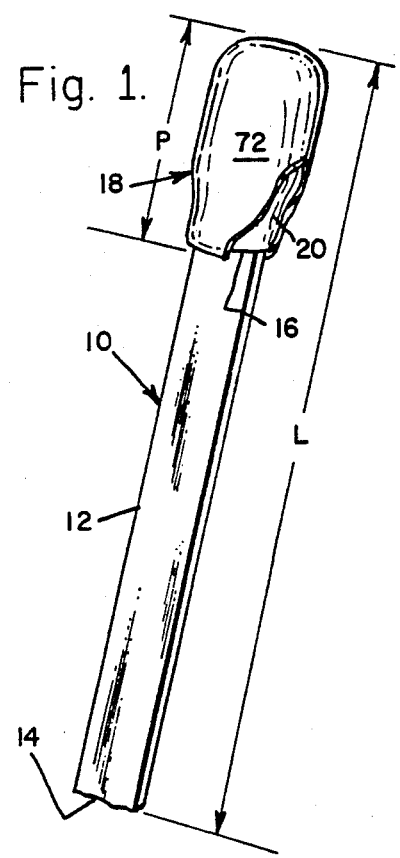
FIG. 1 is an enlarged view of a single breath freshening pick.

Referring particularly to FIG. 1, there is illustrated at 10 a single freshening elongated member of the present invention. The freshening pick 10 comprises an elongated stem section 12 having a first end 14 and a second end 16. Adjacent the second end 16, the stem supports a freshener retaining means 18 which is a swab made of absorbent material. By way of example, the overall length "L" of the entire stem 12 may be approximately 1¼ inches while the length "p" of the freshener retaining means 18 may be approximately ¼ inch. Of course other lengths for both the stem 12 and the freshener retaining means 18 are within the spirit and scope of the present invention. By way of example, the stem may be made of strong thin plastic material such as mylar or cellophane or strong paper material such as thin cardboard, comparable to the stem of a match. The absorbent swab of the freshener retaining means 18 is preferably made of velvet, but may also be made of other absorbent material such as cotton. The swab of the freshener retaining means 18 is impregnated with breath and mouth freshening agents 20. By way of example, the preferred breath and mouth freshening agent is concentrated mouthwash. It is also within the spirit and scope of the present invention to have different flavors of mouthwash on different freshener retaining means 18. In use, the stem section 12 of an individual freshening pick 10 is held adjacent its first end 14 between the thumb and forefinger and placed into the user's mouth. The freshener retaining means 18 is dabbed on the user's tongue and moved between the user's cheek and gums so that the freshening agent 20 may be transferred from the freshener retaining means 18 to the interior of the user's mouth. In this way, the user's mouth is freshened and the user's breath is freshened. After use, the freshening elongated member 10 is discarded.

Figure 2:
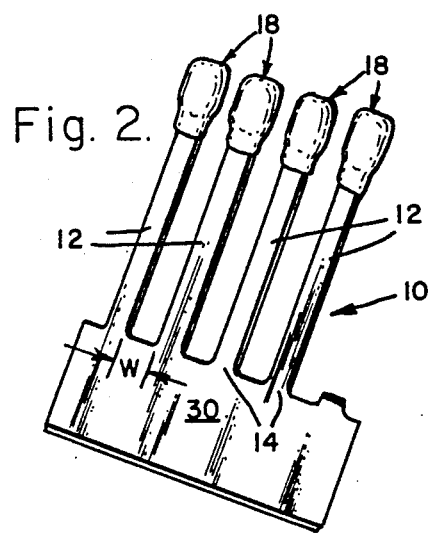
FIG. 2 is a perspective view of a single row of breath freshening elongated members.

Referring to FIG. 2, in the preferred embodiment, a multiplicity of freshening elongated members 10 are aligned adjacent one another and spaced apart from one another by approximately the same distance as the width "W" of each stem 12. The stems 12 are all attached to a common base 30 at their respective first ends 14. In the preferred embodiment, the base 30 and stems 12 are cut from a single sheet of material such as thin plastic. Each stem 12 can be individually torn off from the base 30 when it is desired to use that respective freshener elongated member 10. To assist in the tearing, a score line 32 may be formed at the intersection of the first end of the stem and the base.

Figure 3:
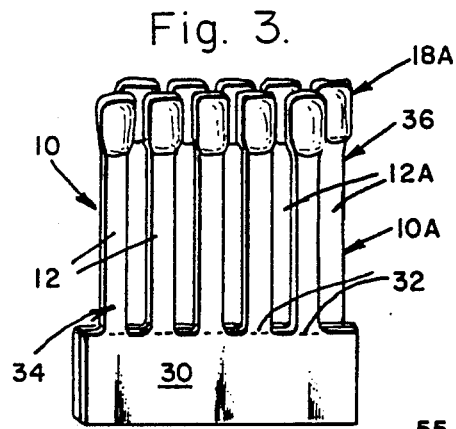
FIG. 3 is a perspective view of two rows of breath freshening elongated members illustrating elongated members in one row offset from picks in the adjacent row.
Figure 4:
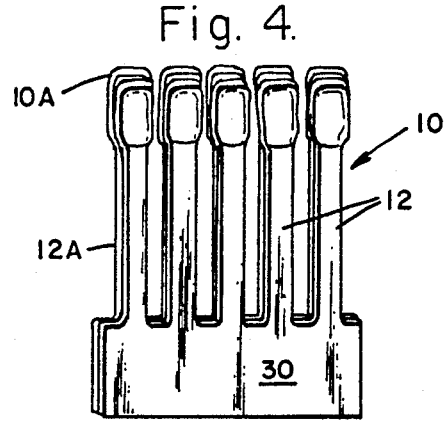
FIG. 4 is a perspective view of two rows of breath freshening elongated members, illustrating elongated members in one row directly aligned with elongated members in the adjacent row.

While the present invention may be utilized with only a single row of freshener elongated members 10, the preferred embodiment utilizes a multiplicity of rows of freshener picks. Referring to FIG. 3, two adjacent rows are illustrated. The freshener elongated members 10 in first row 34 are offset from the freshener elongated members 10A in second row 36 such that the stem 12A and freshener retaining means 18A for each freshener elongated member 10A in row 36 is located in the space between adjacent stems 10 and freshener retaining means 18 in row 34. In this way, the freshening agents 20 from adjacent freshener elongated members 10 do not come directly in contact with one another. Of course it is within the spirit and scope of the present invention to have the adjacent rows of freshening picks aligned so that elongated members in one row are directly aligned with picks in the adjacent row, as illustrated in FIG. 4.

Figure 5:
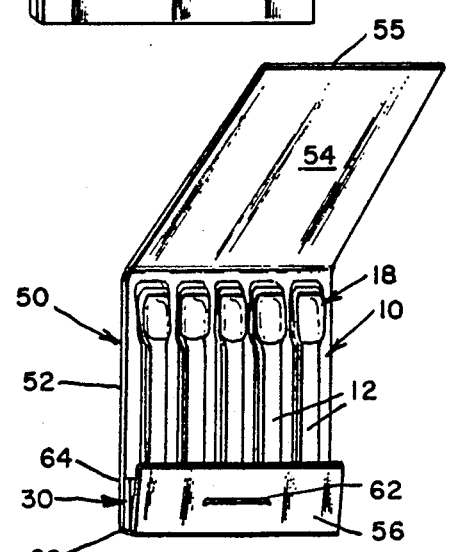
FIG. 5 is a perspective view of the present invention compact mouth and breath freshening apparatus with the cover in the opened position to illustrate a multiplicity of mouth and breath freshening elongated members retained therein.

The entire multiplicity of rows of freshener elongated members are retained within a container. Referring to FIG. 5, a compact container 50 is formed in a matchbook configuration. The container 50 is made of one piece construction and comprises a rear wall 52 which extends at one end into a foldover cover 54. At the other end, the rear wall 52 extends into a flipover flap 56. The base 30 or multiplicity of bases in the event several rows of freshener elongated members 10 are retained is held between the rear wall 52 and the flipover flap 56 and mean be affixed therebetween by suitable retaining means such as glue 60, staples 62, etc. The foldover cover 54 has an open edge 55 which may be inserted into the space 64 between the flipover flap 56 and adjacent base 30 to thereby close the container 50 in a manner comparable to closing a matchbook. It will be appreciated that this cover arrangement is only one of numerous cover arrangements which are within the spirit and scope of the present invention.

Figure 6:
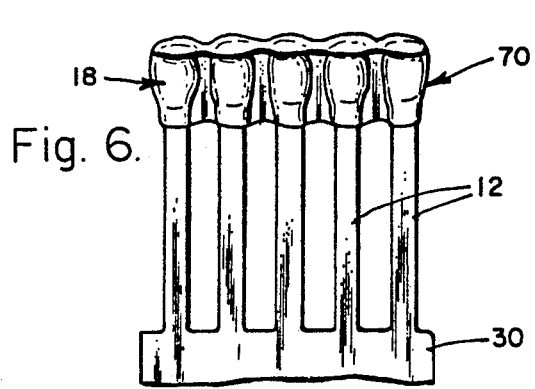
FIG. 6 is a perspective view of a single row of breath freshening elongated members with the freshener retaining means covered by a wrapping or sealing member.

Referring to FIG. 6, to help retain the freshness of the freshening agents 20, the freshener retaining means 18 may be housed in a wrapper or sealing member 70 which by way of example may be a plastic envelope which extends along each row of freshener elongated members and covers the freshener retaining means 18 of each freshener elongated member 10 in the row. It is also within the spirit and scope of the present invention to have the freshener retaining means 18 of each individual freshener pick 10 individually wrapped, as illustrated by the individual wrapping 72 in FIG. 1. When a specific freshener pick is desired for use, the wrapping can be torn off an individually wrapped elongated member or the elongated member can be torn away from the portion of wrapper or sealing member 70 covering it and thereafter torn off the base.

As a supplemental benefit, advertising and other promotional printing may be placed on the surfaces of the container.

The alternative embodiment of the present invention is illustrated in FIGS. 7 through 11. Referring particularly to FIGS. 7 through 9, there is illustrated at 80 a single freshening elongated member of the present invention. The freshening pick 80 comprises an elongated stem section 82 having a first end 84 and a second end 86. Adjacent the second end 86, the stem supports a freshener retaining means 88 which is a swab made of absorbent material. By way of example, the overall length "L'" of the entire stem 82 may be approximately 1¼ inches while the length "p'" of the freshener retaining means 88 may be approximately ¼ inch. Of course other lengths for both the stem 82 and the freshener retaining means 88 are within the spirit and scope of the present invention. By way of example, the stem may be made of strong thin plastic material such as mylar or cellophane or strong paper material such as thin cardboard, comparable to the stem of a match. The absorbent swab of the freshener retaining means 88 is preferably made of velvet, but may also be made of other absorbent material such as cotton. The swab of the freshener retaining means 88 is impregnated with breath and mouth freshening agents 20. By way of example, the preferred breath and mouth freshening agent is concentrated mouthwash. It is also within the spirit and scope of the present invention to have different flavors of mouthwash on different freshener retaining means 88. In use, the individual stem 80 is held adjacent its first end 84 between the thumb and forefinger and placed into the user's mouth. The freshener retaining means 88 is dabbed on the user's tongue and moved between the user's cheek and gums so that the freshening agent 20 may be transferred from the freshener retaining means 88 to the interior of the user's mouth. In this way, the user's mouth is freshened and the user's breath is freshened. After use, the freshening pick 80 is discarded.

Referring to FIG. 7, in the alternative embodiment, a multiplicity of freshening elongated members 80 are aligned adjacent one another and spaced apart from one another by approximately the same distance as the width "W'" of each stem 82. The respective freshener retaining means of head 88 are encased in a plastic pouch 90 with a score line separating one freshener retainer means from the adjacent freshener retaining means. In this way, the freshening elongated member 80 is supported by the freshener retaining means 88 and each freshener retainer means is maintained in a sanitary condition by being encased in the plastic pouch. As illustrated in FIG. 7, when it is desired to use an individual elongated member 80, the user holds the stem 82 in his hand and pulls on it, thereby causing the freshener retaining means 88 to be pulled out of its individual wrapper chamber.

While the alternative embodiment is illustrated with only a single row of elongated members, it will be appreciated that as with the first embodiment, the alternative embodiment may also have a multiplicity of rows of elongated members, either aligned with each other comparable to FIG. 4 or offset from one another comparable to FIG. 3.

Referring to FIGS. 7, 10 and 11, the freshener elongated members 80 are retained within a container. A compact container 100 is formed in a matchbook configuration. The container 100 is made of one piece construction and comprises a rear wall 102 which extends at one end into a foldover cover 104. At the other end, the rear wall 102 extends into a flipover flap 106. The plastic wrapper or pouch 90 is held between the rear wall 102 and the flipover flap 106 and can be affixed therebetween by suitable retaining means such as staples 112, etc. The foldover cover 104 has an open edge 105 which may be inserted into the space 114 between the flipover flap 106 and wrapper or pouch 90 to thereby close the container 100 in a manner comparable to closing a matchbook. It will be appreciated that this cover arrangement is only one of numerous cover arrangements which are within the spirit and scope of the present invention.

Defined more broadly, the alternative embodiment is a mouth and breath freshening apparatus comprising: (a) a multiplicity of freshener elongated members; (b) each freshener elongated member further comprising an elongated stem having a first end and a second end with a freshener retaining means supported on the elongated stem adjacent the second end; (c) a wrapper having a multiplicity of individual chambers aligned adjacent one another with a respective one of the freshener retaining means supported and sealed within a respective one chamber of the wrapper such that the stem end of each freshener elongated member extends away from the wrapper and each respective first end is remote from the wrapper; (d) each freshener retaining means is impregnated with a mouth and breath freshening agent. In addition, said multiplicity of freshener elongated members and wrapper are supported within a container. The container is of a matchbook configuration comprising a rear wall which extends at one end into a foldover cover and which extends at its other end into a flipover flap and the wrapper is retained between the rear wall and the flipover flap such that the stems are aligned between the rear wall and the foldover cover.

The present invention, in all of the embodiments, provides many significant advantages. The freshening agent can be a liquid or a gel. The user does not need privacy because the unique dispensing means makes it go unseen (with aerosols you have to open your mouth and with drops in a bottle you need to stick your tongue out, so it cannot be used but in privacy. You can offer another person an individual stick because it is a discreet self contained unit. The individual sticks can contain different flavors in a single packet. The present invention is much less expensive to produce than a bottle or aerosol dispenser. The present invention can be offered in a restaurant after a meal because of its inexpensive cost and sanitary manner. There is no sugar and it is not necessary to keep it in your mouth like a breath mint.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus is intended only for illustration and for disclosure of an operative embodiment and not to show all of the various forms of modification in which the invention might be embodied or operated.

The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:

1. A mouth and breath freshening apparatus comprising:

7 a. a multiplicity of freshener elongated members;
b. a supporting means;
c. each freshener elongated member further comprising a freshener retaining means impregnated with a mouth and breath freshening agent, and an elongated step having a first end generally embedded in the freshener retaining means and a second end attached to said supporting means such that said multiplicity of freshener elongated members are aligned in a row; and
d. a sealing means covering said freshener retaining means of each freshener member, the sealing means having a multiplicity of individual chambers aligned adjacent one another, where the freshener retaining means of a respective freshener elongated member is placed within an individual chamber such that the stem of the respective freshener elongated member extends away from the chamber.

2. A mouth and breath freshening apparatus in accordance with claim 1 wherein said stem of each freshener elongated member is made of thin plastic material.

3. A mouth and breath freshening apparatus in accordance with claim 1 wherein said freshener retaining means of each freshener elongated member is made of absorbent material.

4. A mouth and breath freshening apparatus in accordance with claim 3 wherein said freshener retaining means of each freshener elongated member is made of velvet.

5. A mouth and breath freshening apparatus in accordance with claim 1 wherein said mouth and breath freshening agent is concentrated mouthwash.

6. A mouth and breath freshening apparatus in accordance with claim 1 further comprising a container for retaining said multiplicity of freshener elongated members and said supporting means.

7. A mouth and breath freshening apparatus in accordance with claim 6 wherein said container has a back which extends at its one end into a foldover cover and at its opposite end into a flipover flap, whereby said supporting means is affixed between the back and the flipover flap of said container.

8. A mouth and breath freshening apparatus comprising:
a. a multiplicity of freshener elongated members comprising the freshener elongated members of a first subset and the freshener elongated members of a second subset;
b. a first and a second supporting means;
c. each freshener elongated member further comprising a freshener retaining means impregnated with a mouth and breath freshening agent, and an elongated stem having a first end generally embedded in the freshener retaining means and a second end;
d. the second end of each of the stems of the freshener elongated members of said first subset are attached to said first supporting means, and aligned in a row and spaced apart from one another;
e. the second end of each of the stems of the freshener elongated members of said second subset are attached to said second supporting means, and aligned in a row and spaced apart from one another;
f. a container made of a sheet material having a generally rectangular shaped flat back which extends at its one end into a foldover cover and at its opposite end into a flipover flap; and

8 g. a first sealing means covering all freshener retaining means of the freshener members of said first subset, and a second sealing means covering all freshener retaining means of the freshener members of said first subset, and a second sealing means covering all freshener retaining means of the freshener members of said second subset;
h. whereby said first and second supporting means are affixed between the back and the flipover flap of said container.

9. A mouth and breath freshening apparatus in accordance with claim 8 wherein said sealing means has a multiplicity of individual chambers aligned adjacent one another, where the freshener retaining means of a respective freshener elongated member is placed within an individual chamber such that the stem of the respective freshener elongated member extends away from the chamber.

10. A mouth and breath freshening apparatus in accordance with claim 8 wherein said stem of each freshener elongated member is made of thin plastic material.

11. A mouth and breath freshening apparatus in accordance with claim 8 wherein said freshener retaining means of each freshener elongated member is made of absorbent material.

12. A mouth and breath freshening apparatus in accordance with claim 8 wherein said mouth and breath freshening agent is concentrated mouthwash.

13. A mouth and breath freshening apparatus in accordance with claim 8 wherein said first and second supporting means are placed adjacent one another such that the freshener elongated members of said first subset are offset from the freshener elongated members of said second subset.

14. A mouth and breath freshening apparatus in accordance with claim 8 wherein said first and second supporting means are placed adjacent one another such that the freshener elongated members of said first subset are adjacent the freshener elongated members of said second subset.

15. A mouth and breath freshening apparatus comprising:
a. a multiplicity of freshener elongated members;
b. each freshener elongated member further comprising a freshener retaining means impregnated with a mouth and breath freshening agent, and an elongated stem having an end generally embedded in the freshener retaining means; and
c. a sealing means covering said freshener retaining means of each freshener elongated member, the sealing means having a multiplicity of individual chambers aligned adjacent one another, where the freshener retaining means of a respective freshener elongated member is placed within an individual chamber such that the stem of the respective freshener elongated member extends away from the chamber.

16. A mouth and breath freshening apparatus in accordance with claim 15 wherein said stem of each freshener elongated member is made of thin plastic material.

17. A mouth and breath freshening apparatus in accordance with claim 15 wherein said freshener retaining means of each freshener elongated member is made of absorbent material.

18. A mouth and breath freshening apparatus in accordance with claim 17 wherein said freshener retaining means of each freshener elongated member is made of velvet.

19. A mouth and breath freshening apparatus in accordance with claim 15 wherein said mouth and breath freshening agent is concentrated mouthwash.

20. A mouth and breath freshening apparatus in accordance with claim 15 further comprising a container for retaining said multiplicity of freshener elongated members.

21. A mouth and breath freshening apparatus in accordance with claim 20 wherein said container has a back which extends at its one end into a foldover cover and at its opposite end into a flipover flap, whereby said sealing means is affixed between the back and the flipover flap of said container such that the stems of said multiplicity of freshener elongated members are aligned between the back and the foldover cover of said container.

* * * * *